United States Patent

Mesek et al.

[11] 4,045,833
[45] Sept. 6, 1977

[54] ABSORBENT BED PAD

[75] Inventors: Frederick K. Mesek, Downers Grove; Virginia L. Repke, Oak Forest, both of Ill.

[73] Assignee: Johnson & Johnson, New Brunswick, N.J.

[21] Appl. No.: 582,479

[22] Filed: May 30, 1975

Related U.S. Application Data

[63] Continuation of Ser. No. 386,114, Aug. 6, 1973, abandoned.

[51] Int. Cl.² .................................. A61F 13/16
[52] U.S. Cl. ............................... 5/335; 128/287
[58] Field of Search .............. 128/284, 296, 287; 19/145.5, 156.3, 156.4; 156/62.2, 244, 290, 291; 161/151, 146, 148, 410; 5/335, 355

[56] References Cited

U.S. PATENT DOCUMENTS

| 2,152,901 | 4/1939 | Manning | 154/33 |
| 3,065,751 | 11/1962 | Gobbo, Sr. et al. | 128/287 |
| 3,426,756 | 2/1969 | Romanek | 128/287 |
| 3,521,624 | 7/1970 | Gander et al. | 128/132 |
| 3,523,536 | 8/1970 | Ruffo | 128/287 |
| 3,535,187 | 10/1970 | Wood | 156/370 |
| 3,740,797 | 6/1973 | Farrington | 19/156.3 |
| 3,763,863 | 10/1973 | Mesek et al. | 128/287 |
| 3,768,118 | 10/1973 | Ruffo | 19/156.3 |

Primary Examiner—Casmir A. Nunberg

[57] ABSTRACT

An absorbent bed pad comprises a liquid-impervious sheet which is adhered to an absorbent fabric throughout the interface therebetween. The fabric is unitary and highly stable and is formed from a mixture of long and short fibers. The mixture of fibers varies throughout the depth of the fabric to produce a short fiber-enriched face to be adhered to the impervious sheet and a long fiber-enriched face at the outer face. The fabric is through-bonded and may be adhered by adhesive to the backing sheet to produce compaction of the short fiber-enriched face.

In other embodiments the fabric may be treated to increase the wettability of selected portions and a highly compacted, densified layer may be formed integral with the short fiber-enriched face.

The method of producing the bed pad of the invention includes the adherence of the backing sheet to the short fiber-enriched face of the fabric by the application of adhesive or by the direct extrusion of the backing sheet onto the short fiber-enriched face without the use of adhesive.

12 Claims, 9 Drawing Figures

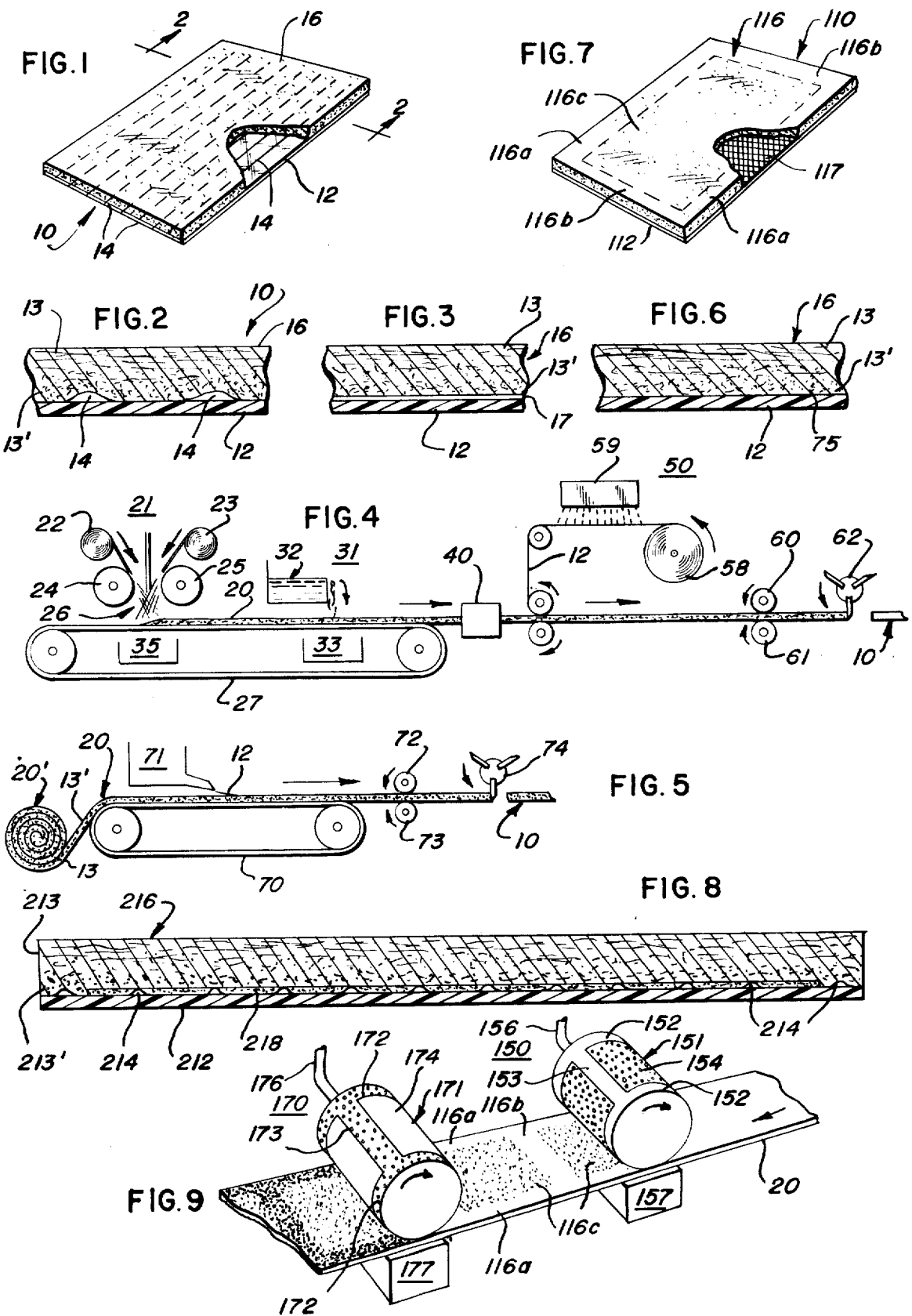

ABSORBENT BED PAD

This is a continuation of application Ser. No. 386,114, filed Aug. 6, 1973.

BACKGROUND OF THE INVENTION

This invention relates to an improved absorbent bed pad and the method for producing these pads. Many different bed pad constructions have been proposed and used, and some have met with widespread commercial success, in spite of certain inadequacies and functional properties.

Typically, prior art absorbent bed pads have been formed with three components, a liquid-impervious backing sheet, an absorbent structure centrally disposed on the backing sheet, and a water-pervious facing sheet disposed over the absorbent panel or batt. The absorbent panel is generally a nonwoven layer composed of short paper making fibers which are less costly than long or textile fibers, but which also have a tendency to dust. The facing layer is therefore designed to contain the short fibers of the panel within the bed pad to prevent dusting.

One of the most serious prior art problems has been the inability to provide a suitable construction that will maintain its integrity during use. Specifically, the facing layer of the prior art bed pads tends to tear under the weight of the patient during use due, in part, to the added liquid weight deposited in the pad and the comparatively large width of the pad. Since the facing layer is generally only adhered to at its margins to the backing sheet, the facing layer has little reinforcement and may be shifted during movement of the patient which increases the possibility of tearing. As a result, prior art absorbent bed pads are limited in width size to provide facing layer stability.

In addition to the above problems, since the facing layer is generally adhered only to the marginal side portions of the backing sheet and the absorbent panel is discontinuously adhered to the backing sheet, voids can be created between the components of the bed pad during use which results in a pooling of body fluid in the voids. In some prior art bed pads, the water-impervious backing sheet is folded over the facing layer along the marginal side portions and end portions so that the impervious sheet, generally made from a plastic, may come into contact with a patient's skin and possibly cause irritation and infection.

SUMMARY OF THE INVENTION

In accordance with the present invention, a bed pad is formed by the combination of an impervious backing sheet joined to a unitary nonwoven fabric having different concentrations of long and short fibers throughout its thickness which provides advantageous functional characteristics of improved feel and comfort with high tensile strength or structural stability and pad integrity at low cost.

Fibers are usually classified according to length, with relatively long or textile length fibers being longer than about ¼ inch and generally between ½ and 2½ inches in length. The term "long fibers", as used herein, refers to textile length fibers having a length greater than ¼ inch and the fibers may be of natural or synthetic origin. The term "short fibers", as used herein, refers to paper making fibers, such as wood pulp fibers or cotton linters having a length less than about ¼ inch. While it is recognized that short fibers are usually substantially less costly than long fibers, it is also recognized in many instances that it is desirable to strengthen a short fiber product by including a blend of long fibers therein.

Nonwoven materials are structures which in general consist of an assemblage or web of fibers, joined randomly or systematically by mechanical, chemical or other means. These materials are well known in the art, having gained considerable prominence within the last 25 years or so in the consumer market, industrial-commercial market and in the hospital fields.

The bed pad of the present invention is formed by adhering an impervious backing sheet to a pulp-enriched face of a fabric comprising a mixture of long and short fibers at an overall concentration. The fabric is enriched with respect to long fibers in excess of the overall concentration at its outer face to provide stability, and to minimize the cost and provide enhanced wettability characteristics, the inner face of the fabric is enriched with respect to short fibers in excess of the overall concentration. Within the fabric, the concentrations of long and short fibers decrease at increasing distances from their enriched faces to provide a transition region within the fabric. The decrease in fiber concentration from one face to another face takes place throughout the fabric, which is to say that there is no sharp interface between one fiber concentration and another, and that the concentration of a particular fiber at any depth is less than the concentration at a depth closer to one face and more than its concentration at a depth closer to the opposite face, although not necessarily by the same amount. The fibers in the fabric portion of the bed pad are through-bonded to provide a structural integrity throughout the fabric and may be selectively treated to enhance the wettability and wicking actions in these areas of the fabric.

The impervious backing sheet utilized in the present invention may be either of the preformed embossed type, which may be glued to the fabric throughout the interface therebetween, or the sheet may be extruded directly on to the pulp-enriched face of the fabric. With either type of backing sheet the unitary facing layer is reinforced by its adherence thereto so that the bed pad is quite stable and not limited as to width. Preferably, the backing sheet is formed from "medium density" polyethylene, as is known in the art, which provides the desired degree of conformability and yet allows the pad to remain in position during use. The preformed embossed polyethylene film may be adhered to the pulp-enriched face of the fabric by means of adhesive distributed in either a discontinuous or continuous manner. When the latter type of distribution is utilized, the continuous glue coating between the backing sheet and fabric produces some compacting of the pulp fibers at the face of the fabric which results in improved wicking action at the lower depth of the fabric so that body fluids may be spread laterally therein. In a similar manner, by extruding medium density polyethylene onto the pulp-enriched face of the fabric, some compacting of the short fibers is produced.

The bed pad of the present invention may be most conveniently formed by first air laying fibers to produce a web of the type described above, subsequently through bonding the fibers in the web to form a fabric and then either bonding to its pulp-enriched face a medium density, preformed embossed polyethylene film with an adhesive, or extruding onto its pulp-enriched face a polyethylene film.

Recent improvements have been made in air laying techniques, such as, for example, the improvements disclosed and claimed in commonly assigned, copending Ruffo et al application Ser. No. 108,546, filed Jan. 21, 1971, now U.S. Pat. No. 3,768,118 and in its divisional application Ser. No. 358,793, filed May 9, 1973 now abandoned, the disclosures of which are hereby incorporated by reference.

Briefly, one of the air laying techniques disclosed in Ruffo et al and utilized as a preferred technique in the method of this invention for forming the absorbent fabric includes the steps of feeding fibers of two different types, such as short and long fibers, to separate fiber openings at given rates to provide in the fabric a given overall concentration of long and short fibers, individualizing the fibers from the separate fiber sources, suspending the fibers from each source in separate gaseous streams, and impelling the gaseous streams at least initially towards one another and combining the gaseous streams to form a combined gaseous carrier stream. At gas-to-fiber volume ratios above 12,000:1, the fibers in the individual gaseous streams are spaced sufficiently from one another so that if the gaseous streams are impinged upon each other without substantial diminution in their velocities, fibers of each gaseous stream will cross over the oncoming fibers of the other gaseous stream to form, upon deposit of the fibers, a nonwoven web which is characterized by a concentration of long fibers on one face in excess of the overall concentration and a concentration of short fibers on the other face in excess of the overall concentration, with a transitional zone between the faces in which the concentration of long and short fibers gradually diminishes away from the face having the maximum concentration to the opposite face. This process of forming the fabric web provides a shingling of fibers during the air laying process which, together with the controlled binder applications discussed below, cooperates with the short and long fiber distribution in the fabric to maintain structural integrity therein.

The preferred fabric, referred to as a "transition" fabric, is then combined in laminar fashion with its pulp-enriched face in juxtaposition with the impervious backing sheet to produce one form of this invention.

After the transition fabric has been formed, it may be immediately joined with the impervious backing sheet in the same production line or may be rolled for subsequent use in another production line for backing sheet adherence. In either method, the backing sheet may be provided from a roll of preformed, embossed, medium density, polyethylene film which is adhered to the pulp-enriched face of the fabric by either lines of adhesive or a continuous coating of adhesive. Alternately, the medium density polyethylene may be extruded onto the pulp-enriched face of the fabric, and when this method is utilized, no adhesive is necessary since the extruded plastic is self-bonding to the pulp fiber-enriched face of the fabric.

A further modification may also be utilized in forming the fabric in which an integral, highly compacted, paper-like, densified layer is formed on the pulp enriched face of the fabric. This densified layer functions to increase the wicking action of the fabric face in juxtaposition with the backing sheet and is preferably formed in the central area portion of the fabric so that body liquids will not be wicked to the edges of the bed pad. A still further modification, which may also be utilized, alone or in combination with the last mentioned modification, provides for the selective application of wetting agent and/or liquid repellent binder to produce greter liquid wettability in the central area portion of the bed pad and water repellent boundaries along at least the side marginal edges thereof.

BRIEF DESCRIPTION OF THE DRAWINGS

FIG. 1 is a perspective view, with certain portions broken away, of a bed pad in accordance with one aspect of this invention;

FIG. 2 is an enlarged partial cross section of the bed pad of FIG. 1 taken generally along line 2—2;

FIG. 3 is an enlarged partial cross section, similar to FIG. 2, illustrating an alternate embodiment utilizing a uniform adhesive layer;

FIG. 4 is a simplified schematic view of the production line on which the bed pad of the invention is made utilizing preformed polyethylene film;

FIG. 5 is a simplified schematic view of a production line for producing a bed pad of this invention with an extruded backing sheet;

FIG. 6 is an enlarged partial cross section view, similar to FIG. 2, illustrating a bed pad with an extruded backing sheet;

FIG. 7 is a perspective view, with certain portions broken away, illustrating a modified bed pad;

FIG. 8 is an enlarged partial cross section of another modified bed pad; and

FIG. 9 is a perspective view illustrating an alternate binder applying means utilized in the production line of FIG. 1, and suitable for the production of the bed pad of FIG. 7.

DETAILED DESCRIPTION

While this invention is susceptible of embodiment in many different forms, there is shown in the drawings and will herein be described in detail a preferred embodiment of the invention and modifications thereof, with the understanding that the present disclosure is to be considered as an exemplification of the principles of the invention and is not intended to limit the invention to the embodiments illustrated. The scope of the invention will be pointed out in the appended claims.

Referring to the drawings, and particularly to FIGS. 1 and 2, the bed pad assembly 10 comprises a lowermost water-impervious sheet 12 which is rectangular in shape, and an overlaying absorbent fabric 16 of fibrous material, which is also rectangular in shape, equal in dimension, and coterminous with the impervious sheet and in contact therewith throughout the interface therebetween. The absorbent fabric 16 is adhered to the impervious sheet by spaced bead lines 14 of adhesive extending substantially throughout the interface therebetween.

In the preferred embodiment of the invention, moisture-impervious sheet 12 is formed of medum density polyethylene, as is known in the art, having a thickness of approximately 1 mil. The sheet may be smooth, or it may be embossed to improve its strength and feel. As will be described in greater detail below, the impervious sheet may be provided from a preformed roll of embossed medium density polyethylene, or may be extruded, directly onto the absorbent facing layer fabric.

The fabric 16 is preferably formed by utilizing an air laying process, such as, for example, the process disclosed in the above-mentioned Ruffo et al. application, to produce a transition fabric having opposed outer major faces 13 and 13'. Face 13 is comprised of a greater amount by weight of long fibers and a lesser amount by weight of short cellulosic fibers as compared with the overall concentration of these fibers in the fabric) interspersed and blended therewith. Face 13' is comprised of a greater amount by weight of short cellulosic fibers and a lesser amount by weight of long fibers (as compared to the overall concentration of these fibers in the fabric) interspersed and blended therewith. The term face, as used herein, means that portion of the fabric layer which extends inwardly from one major surface to approximately ¼ of the total cross-sectional thickness of the fabric layer. The transition of fiber concentration between faces 13 and 13' is characterized by decreasing concentrations of textile length fabrics from the outer face 13 to the inner face 13'.

The overall concentration of textile length fibers within fabric 16 may vary from about 2% to about 50%, preferably from about 10% to about 25% with the remainder being made of short fibers. Textile length fibers may, for example, be 1.5 denier rayon fibers uniformly cut to 1¼ inches in length, although the present invention is not limited to specific textile length fiber or concentration thereof. For example, in fabrics with the overall concentration of textile length fibers being from about 10% to about 25% by weight, it has been found that the concentration of textile length fibers at face 13 is about 5% to 20% by weight higher than the overall concentration. In a specific embodiment of fabric 16, which had an overall composition of about 25% by weight rayon fibers and about 75% by weight short cellulosic fibers, the concentration of rayon fibers at face 13 was approximately 35% to 40% and the textile length fibers were substantially uniformly blended with 65-60% of short cellulosic fibers. In this last-mentioned fabric embodiment, approximately 5-10% of rayon fibers were present at face 13', and were in uniform admixture with about 95-90% of short cellulosic fibers.

As illustrated in FIG. 4, the bed pad of this invention is formed by air laying fibers to produce the transition fabric and then joining the pulp-enriched face of the fabric to a water-impervious backing sheet. The absorbent fabric 16, as described above, is preferably formed in accordance with the process disclosed in the abovementioned Ruffo et al. application. The absorbent fabric 16 has an overall concentration of short fibers, not exceeding about ¼ inch in length, the average short fibers are from about 1/16 inch to about 3/16 inch in length. The fabric is prepared initially at position 21 by feeding a supply of short cellulosic fibers 22 and a supply of textile length fibers 23 to a fiber opening and mixing apparatus 26, which takes the form of two individual rotating lickerins 24 and 25, as described in the abovementioned Ruffo et al. application. Fibers 22 and 23 are fed to the opening means 24 and 25, respectively, at a desired rate to provide a web 20 with a desired overall fiber concentration. Apparatus 26, in addition to opening fiber sources 22 and 23 and individualizing the fibers, also suspends the fibers from each source in separate gaseous streams which are impelled toward one another and combined to form a carrier gaseous stream wherein the fibers from each separate stream cross over one another. In this arrangement, the fibers from lickerin 25 tend to be deposited on an upstream portion of the foraminous belt 27 and the fibers from lickerin 24 tend to be deposited further downstream on the previously deposited fibers from lickerin 25. The deposited fibers are condensed on the belt 27 by suction box 35 which pulls air, as by suction fans, at a high velocity, through the belt 27 and deposited fibers. Web 20 is characterized by a major face 13 adjacent to belt 27 enriched in long fibers and a second major face 13' enriched in short fibers with the concentration of long and short fibers decreasing at increasing distances from their enriched faces.

Fabric layers suitable for use in this invention have weights in the range of 2 to 5 oz./yd.$^2$ and most preferably within the range of 2.25 to about 2.75 oz./yd.$^2$.

After the fibers have been deposited, the web is treated with a bonding agent, such as a self-cross-linking acrylic emulsion, and the fabric is also treated with a wetting agent, or surfactant, to partially counteract the water repellency of the bonding agent and to bring the fabric to the desired degree of wettability. One bonding agent which has been employed with considerable success is a latex of polyethylene-acrylate copolymer containing small amounts of acrylonitrile and a cross-linking monomer sold under the trade name HYCAR 2600 × 120. The bonding agent should preferably be of the low viscosity type with a viscosity of less than 5 centipoises. To avoid excess water repellency, a surfactant, preferably a nonionic surfactant, is included in the binder solution. A typical surfactant which has been found to be suitable is the nonionic surfactant polyethylene sorbitan monolaurate sold under the trademark TWEEN 20. In a typical application, the binder solution is controlled to give the fabric a dry solids add-on in the range of from about 4½% to 9% based on the fabric weight, of which from about 0.15% to about 0.30% is the amount of surfactant. In fabric layers having an extremely low percentage of long fibers, such as in fabric layers approaching 2% of long fibers, the binder amount would be toward the high side of the abovementioned range. It will be understood that the above-mentioned surfactants moderate and reduce the water repellency which may be imparted to the short and long fibers of the web by the bonding agent which bonds them into an integral layer. The web 20 is through-bonded by carrying it on conveyor 27 to a binding station 31 where it may be throughbonded by a binder agent of the type described from source 32. The binder is deposited on one face of web 20 from source 32 and the web then passes over a suction source 33 which draws the binders through the web and removes any excess binder solution.

The web 20 is then dried by passing through the drying station shown schematically at 40. The drying station is selected by balancing various criteria including the desired degree of binder fixation of the fibers within the web and the structural integrity to be imparted to the outer faces of the fabric. In the drying of a web by the application of heat to the web surfaces, there is a tendency for the binder solution to migrate toward the heat source as the water carrier is evaporated. Reliance on surface heating as the sole means of drying may cause sufficient binder migration to adversely affect the strength of the interior of the web. It is, therefore, sometimes preferred that a portion of the heating action be carried out in a manner which makes heat available to the interior of the web, such as dielectric heating, infrared heating, or heating by a strong current of hot air which brings heat to the interior of the web by convection. In order to achieve a balance between surface and interior drying, the drying station may be in two stages: (a) a first stage which is designed to promote a drying action throughout the web, such as those just described; and (b) a second stage which is designed to apply heat to the exterior surfaces of the web, such as a series of alternating rotating steam cans around which the faces of the web are alternately paid.

After the drying process is completed, the web 20 may be wound into a roll for later application of the impervious backing sheet 12, or may pass immediately to a backing sheet application station 50 as illustrated in FIG. 4.

As described above, the backing sheet 12 may be adhered to the absorbent fabric layer 16 by bead lines 14 of adhesive. To avoid the formation of voids between the interface of the impervious sheet and the fabric layer, as well as to reinforce the fabric layer, it is desirable that the bead lines 14 be closely spaced so that voids due to separation at the interface between the backing sheet and fabric layer will not be formed when the bed pad is used. It will be appreciated that body fluids, allowed to accumulate on the impervious sheet without being absorbed in the fabric, may flow on the backing sheet and escape from the edges of the pad.

FIG. 3 illustrates a modification to the bed pad of this invention, in which the fabric layer is adhered to the backing sheet 12 by a continuous coating 17 of glue. Coating 17 of glue not only assures that there will be no separation at the interface of the components of this bed pad but also produces some compacting of the short fibers at face 13' which increases the wicking action of these fibers. This increased wicking provides a transport mechanism for spreading body fluids to an increased area of the bed pad at a plane of the fabric opposite the face which is in contact with the patient.

Referring now to FIG. 4, medium density embossed polyethylene film 12 is fed to the assembly from roll 58. Applicator 59 applies adhesive as by parallel lines 14 or as a continuous layer 17 between the polyethylene film and the absorbent fabric layer. The adhesive may also be applied in other patterns, such as spaced dots or other forms of so-called "island" bonds, but fairly close overall adhesion between the backing sheet and the absorbent fabric layer is required and no portion of the polyethylene should be more than about 2 inches from a point of adhesion.

After the fabric web 20 and polyethylene 12 are brought into contact, the assembly is subjected to compression by rolls 60 and 61, and the individual bed pads 10 are cut off by cutter 62.

As indicated above, the impervious backing sheet 12 may also be extruded directly on to the pulp-enriched face 13' of the absorbent fabric layer. This extrusion may take place immediately after formation of the web 20 or may take place on a separate production line. FIG. 5 illustrates a separate schematic production line in which a roll 20' of transition fabric 20 is fed onto conveyor 70 so that the long fiber-enriched face 13 is adjacent the surface of the belt and the short fiber-enriched face 13' is facing upwardly. Belt 70 carries the fabric 20 beneath an extruder 71 which extrudes a layer 12 of medium density polyethylene onto the pulp-enriched face 13' of the fabric. The web then passes between the nip of rollers 72 and 73 which subject the assembly to compression, and the individual bed pads 10 are then cut off by cutter 74.

Similar to the application of a continuous layer of glue, described above, the application of extruded medium density polyethylene causes some compaction of the short fiber enriched face 13' of the fabric layer 16. FIG. 6 illustrates the compacted fibers 75 at face 13' which increase the wicking action of face 13' so that body fluids may be distributed more quickly at this face to retard fluid from flowing back to face 13 and thus enhance the rapidity of absorption of the bed pad.

When it is desired to have areas of less wettability at the marginal side edges of the bed pad and at the end edges, as where the bed pad is relatively narrow so that it may be anticipated that body fluids will be quickly wicked to the edges thereof, the binder and wetting apparatus of FIG. 9 may be used in the production line of FIG. 4 in place of station 31.

In this manner, a bed pad 110, FIG. 7, is produced which has a central area 116c of desired wettability and may also include end edges 116b of decreased wettability so that the marginal portions act as a barrier to fluid flow within the absorbent fabric layer. In the embodiment illustrated in FIG. 7, fabric layer 116 is adhered to impervious backing sheet 112 by means of a continuous coating of adhesive 117.

Referring now to FIG. 9, the system includes two spaced apart through-printing assemblies 150 and 170. Assembly 150 is designed to through print a mixture of binder and surfactant of the types described above, onto the central area portion of the web 20 to provide rectangular area 116c which has the desired wettability for the portions of the fabric layer through which body fluid must pass. To this end, roller 151 is provided which rotates in the direction of web feed (downward to the left as shown in FIG. 9). Roller 151 is hollow and contains a small quantity of the desired binder-surfactant mixture, maintained at a low level therein by continuous supply through line 156. The cylindrical surface of roller 151 comprises solid areas 152 and 153 corresponding respectively to the side 116a and end 116b margins of lesser wettability desired in fabric layer 116 and perforated areas 154 corresponding to rectangular area 116c on the fabric layer. Suction box 157 is below the web where it is in contact with roller 151 and helps pull the binder-surfactant mixture through the perforations in area 154 and through the web 20 when the perforations are under the shallow pool of liquid and over the web. As the web emerges frm under roller 151 it is wet with the binder-surfactant mixture in the areas 116c and dry in the areas 116a and 116b.

Roller 171 in assembly 170 serves to apply binder without surfactant to the areas left dry by roller 151. Roller 171 is also hollow and contains a shallow pool of a binder composition, as described above, provided by line 176. The cylindrical surface of roller 171 is the complement to the cylindrical surface of roller 151 in that the latter is solid in area 174 corresponding to area 116c on the web and is perforated in areas 172 and 173 corresponding to the side and end margins of the facing layer.

Rotating roller 171 cooperates with suction box 177 to wet the previously unwetted portions of the web with the water repellent binder solution to produce, after drying and cutting, the desired marginal areas 116a and 116b of FIG. 7 having lesser wettability than the remainder of the fabric layer.

When it is desired to produce a fabric layer having lesser wettability along the side marginal portions 116a only, the transverse section 153 on roller 151 would be perforated and the transverse section 173 on roller 171 would be eliminated so that only the side marginal portions would be made less wettable than the central portion of the fabric layer.

FIG. 8 illustrates another modification of the bed pad of this invention in which a central rectangular area of the short fiber enriched base 213' has been formed with an integral, highly compacted, densified, paper-like layer or skin 218. The bed pad 210 is other wise similar in structure to that illustrated in FIG. 2 and the various portions are correspondingly marked by the addition of 200 to their numerical designation.

The densified compacted paper-like layer 218 is prepared by moistening the pulp-enriched face of the web 20 with a fine spray of water, and then subjecting the moistened web to pressure. The general method of forming the densified layer 218 is well known in the art, e.g., Burgeni U.S. Pat. No. 3,017,304. While FIG. 8 illustrates the densified layer 218 as being formed in the central portion of the pulp-enriched face 213', the densified layer may also be formed so that it extends completely across the face 213'. The determinaton as to the width of the densified layer 218 depends upon the use to which the bed pad will be put, i.e. relative frequency of changes of the bed pad during use and the anticipated liquid loading. Where it is desirable to have a bordering area at the marginal side edges and end edges of the diaper to act as a boundary or dam against the flow of body fluid from the edges of the bed pad the embodiment illustrated in FIG. 8 is preferred. To form the densified layer 218 in the production line of FIG. 4 a spray nozzle and compression rollers are positioned between drying station 40 and backing sheet applicator station 50. One roller is positioned beneath the web 20 and is provided with a cylindrical surface corresponding in width to that of the web. An upper roller having an enlarged cylindrical central portion corresponding to that which would overlay densified layer 218 is provided to form the densified layer. This latter roller is also provided with a transverse recess corresponding in width to twice the width of end edge barriers to be formed so that no densification takes place therein and the cutter 62 severs the bed pad from the web along a transverse medium line in these non-densified areas.

It will be understood by those skilled in the art that variations and modifications of the specific embodiments described above may be employed without departing from the scope of the invention as defined in the appended claims.

We claim:

1. An absorbent pad comprising: a through-bonded, nonwoven fabric having given overall concentration of long fibers and short fibers, said fabric being enriched in long fibers in excess of said given overall concentration at one face and being enriched in short fibers in excess of said given overall concentration at the other face, and having a transition of fiber concentration between said faces; and a liquid-impervious backing sheet adhered to said short fiber-enriched face throughout the interface therebetween, said fabric face enriched in long fibers being an outermost face of said absorbent pad, said fabric face enriched in long fibers being an outermost face of said absorbent pad.

2. An absorbent bed pad as set forth in claim 1 wherein said backing sheet is coterminous with said fabric and both are rectangular in shape.

3. An absorbent pad as set forth in claim 1 wherein said backing sheet is adhered to said pulp-enriched face by a continuous layer of adhesive.

4. An absorbent pad as set forth in claim 1 wherein the fiber content of said fabric comprises from about 50% to about 98% by weight of short fibers having a fiber length not exceeding $\frac{1}{4}$ inch and from about 2% to about 50% by weight of long fibers having a fiber length of between about $\frac{1}{2}$ and $2\frac{1}{2}$ inches.

5. An absorbent pad as set forth in claim 1 wherein said fabric has a weight in the range of about 2.25 to 2.75 oz./yd.$^2$.

6. An absorbent pad as set forth in claim 1 wherein said fabric further includes a highly compacted, densified, paper-like cellulosic layer at said short fiber-enriched face.

7. An absorbent pad as set forth in claim 1 wherein said fabric is treated with a wetting agent in selected areas to increase the wettability therein as compared to untreated areas.

8. An absorbent pad as set forth in claim 7 wherein said fabric is through-bonded with a binder material which imparts to said fabric a decreased wettability in selected areas as compared to a fabric of unbonded fibers.

9. An absorbent pad comprising: a unitary, porous fabric in the form of a water wettable web of mixed long and short fibers, said fibers being present at a given concentration and having a mixture of fibers throughout its thickness, said mixture varying from a maximum concentration of long fibers at one face to a maximum concentration of short fibers at the other face, with a gradual transition of fiber concentration at increasing distances from said faces, said web being through-bonded and treated with a wetting agent to give it a desired degree of wettability for water in at least the central area portion thereof and a water impervious backing sheet adhered to said web face having a maximum concentration of short fibers throughout the interface therebetween, said fabric face having a maximum concentration of long fibers being an outermost face of said absorbent pad.

10. An absorbent pad as set forth in claim 9 wherein said long fibers are present at an overall concentration from about 10% to about 25% by weight and are present at said long fiber-enriched face in a concentration of from about 5% to 20% by weight higher than said overall concentration.

11. An absorbent pad as set forth in claim 9 wherein said fabric further comprises an integral, highly compacted, paper-like, densified layer at its face in juxtaposition with said backing sheet.

12. The absorbent pad of claim 11 wherein said highly compacted, densified, paper-like layer is formed in the central area portion of said web whereby the marginal end and side portions of said facing layer are used as barriers against fluid flow.

* * * * *